(12) United States Patent  
Dennis

(10) Patent No.: US 6,860,869 B2  
(45) Date of Patent: Mar. 1, 2005

(54) SURGICAL INSTRUMENT SEAL ASSEMBLY

(75) Inventor: William G. Dennis, 11222-4 St. John Industrial Pkwy., Jacksonville, FL (US) 32246

(73) Assignee: William G. Dennis, Ponte Vedra, FL (US)

( * ) Notice: Subject to any disclaimer, the term of this patent is extended or adjusted under 35 U.S.C. 154(b) by 47 days.

(21) Appl. No.: 09/950,274

(22) Filed: Sep. 12, 2001

(65) Prior Publication Data

US 2002/0013552 A1 Jan. 31, 2002

Related U.S. Application Data

(63) Continuation-in-part of application No. 09/885,856, filed on Jun. 20, 2001, which is a continuation of application No. 09/434,608, filed on Nov. 5, 1999, now Pat. No. 6,258,065

(60) Provisional application No. 60/126,356, filed on Mar. 26, 1999.

(51) Int. Cl.[7] ............................................. A61M 5/178
(52) U.S. Cl. ................................................. 604/167.03
(58) Field of Search ..................... 604/164.01, 164.07, 604/167.01, 167.03, 167.04, 167.06; 251/149.1; 285/302

(56) References Cited

U.S. PATENT DOCUMENTS

| | | | |
|---|---|---|---|
| 4,447,237 A | * 5/1984 | Frisch et al. ................ 604/175 |
| 4,929,235 A | 5/1990 | Merry et al. | |
| 4,960,412 A | 10/1990 | Fink | |
| 5,053,013 A | 10/1991 | Ensminger et al. | |
| 5,147,336 A | 9/1992 | Wendell et al. | |
| 5,180,373 A | 1/1993 | Green et al. | |
| 5,269,763 A | 12/1993 | Boehmer et al. | |
| 5,304,143 A | 4/1994 | Green et al. | |
| 5,308,336 A | 5/1994 | Hart et al. | |
| 5,385,553 A | 1/1995 | Hart et al. | |
| 5,391,153 A | 2/1995 | Haber et al. | |
| 5,456,284 A | 10/1995 | Ryan et al. | |
| 5,476,475 A | 12/1995 | Gadberry | |
| 5,492,304 A | 2/1996 | Smith et al. | |
| 5,496,280 A | 3/1996 | Vandenbroek et al. | |
| 5,562,632 A | 10/1996 | Davila et al. | |
| 5,603,702 A | 2/1997 | Smith et al. | |
| 5,628,732 A | 5/1997 | Antoon, Jr. et al. | |
| 5,643,227 A | 7/1997 | Stevens | |
| 5,709,664 A | 1/1998 | Vandenbroek et al. | |
| 5,720,730 A | 2/1998 | Blake, III | |
| 5,727,770 A | 3/1998 | Dennis | |
| 5,741,228 A | 4/1998 | Lambrecht et al. | |
| 5,752,938 A | 5/1998 | Flatland et al. | |
| 5,820,600 A | 10/1998 | Carlson et al. | |
| 5,820,604 A | 10/1998 | Fox et al. | |
| 5,848,997 A | 12/1998 | Erskine et al. | |

* cited by examiner

Primary Examiner—Michael J. Hayes
(74) Attorney, Agent, or Firm—McGuireWoods LLP

(57) ABSTRACT

A surgical seal assembly which forms a seal about a surgical instrument thus preventing the leakage of fluids, gases and the like. The surgical seal assembly includes a valve with a reinforcing layer. The reinforcing layer is preferably a woven fabric and an elastomeric material such as silicon or other similar material. The reinforcing layer expands proportionally with the insertion of the surgical instrument, is tear or puncture resistant and is designed to accommodate off axis alignment and insertion of the surgical instrument.

7 Claims, 5 Drawing Sheets

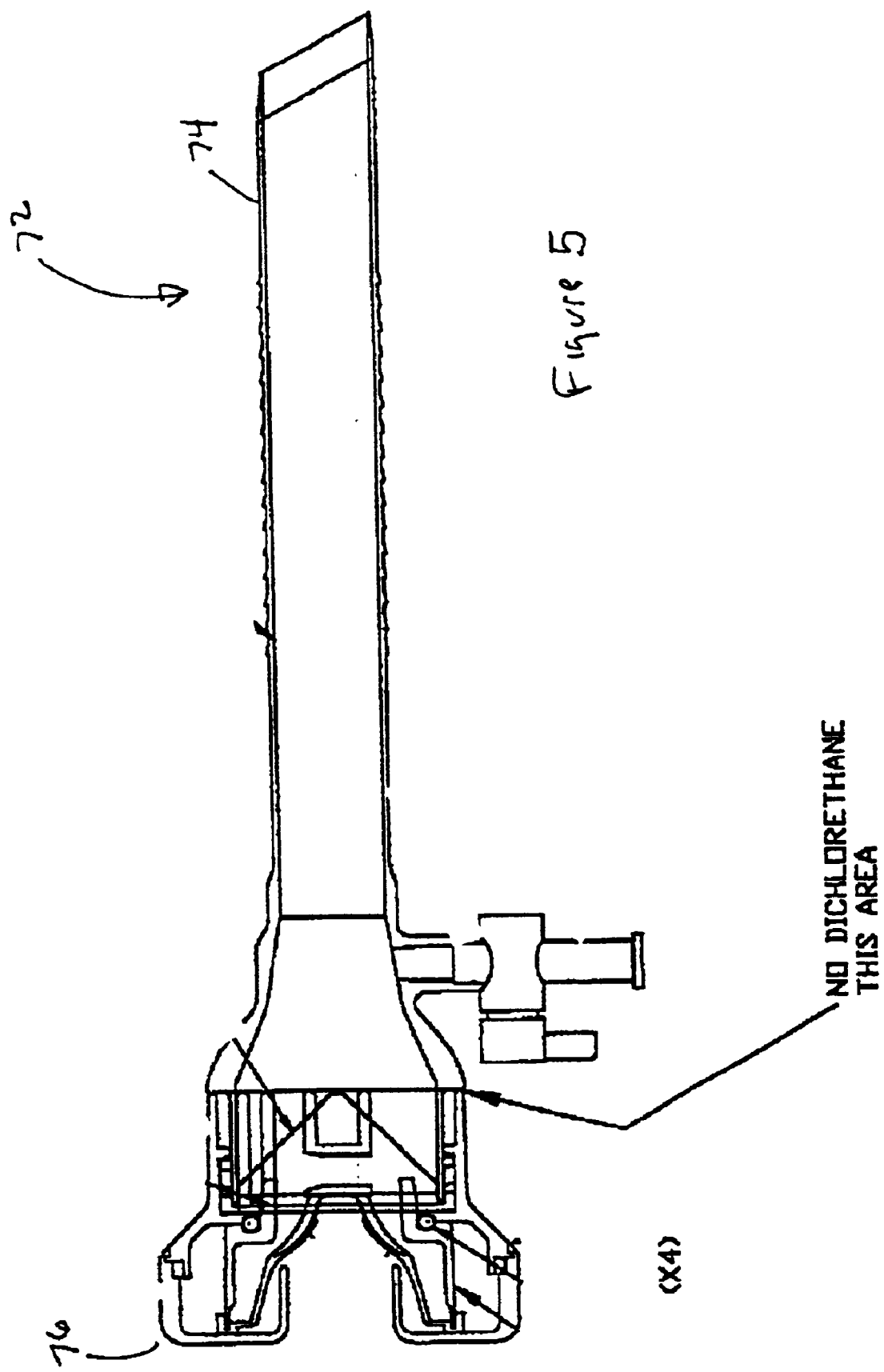

SURGICAL INSTRUMENT SEAL ASSEMBLY

CROSS REFERENCE TO RELATED APPLICATIONS

This application is a continuation-in-part application of co-pending U.S. application Ser. No. 09/885,856, filed on Jun. 20, 2001 which, in turn, is a continuation application of U.S. application Ser. No. 09/434,608, now issued as U.S. Pat. No. 6,258,065. U.S. Pat. No. 6,258,065 claims priority to U.S. provisional application No. 60/126,356 filed on Mar. 26, 1999, all of which are incorporated herein by reference in its entirety.

BACKGROUND OF THE INVENTION

1. Field of the Invention

The present invention relates to a surgical seal assembly and, more particularly to a surgical instrument seal assembly which is capable of maintaining a fluid seal around a surgical instrument.

2. Background Description

In certain types of surgery, a cannula is used to provide a passageway into a body cavity so that a surgical instrument may be passed into that cavity. Cannulas are typically elongate rod-like members having a central bore so that a surgical instrument may be passed through the bore. At times, the body cavity will be insufflated by a gas and at all times, the cannula will be subjected to internal body fluids. Therefore, some form of seal assembly is necessary to allow the surgical instrument to pass through the cannula while maintaining sealed integrity around the instrument such that the insufflation gas, the internal body fluids, or both, cannot escape through the cannula.

In conventional devices, such a seal mechanism includes a housing for mounting on the cannula, with the housing having a bore therethrough for passage of the surgical instrument. Two seals are typically located within the housing. The lower housing contains a seal, typically called a duckbill valve that assists in maintaining gases and fluids in place when an instrument is not inserted within the duckbill valve. The duckbill valve is typically formed from flexible material and includes a slit opening that is capable of deflecting upon insertion of the instrument. The upper housing typically includes a valve seal that includes a relative wide access opening and a relatively narrow valve opening. The valve opening can expand to accommodate the surgical instrument and is resilient to form a seal around the instrument upon insertion.

These conventional seals, however, may not adequately seal the instrument during a surgical procedure. Also, the elastomeric material of the valve seal can be damaged by contact with the surgical instrument upon insertion. As a result, seal protectors have been used. The seal protectors are units separate from the valve seal and are disposed intermediate the seal and the surgical instrument. Some seal protectors include complex lever arrangements that may engage and open the valve opening while acting as a barrier between the instrument and the valve seal. Other approaches include the application of rigid plastic leaf-like members in an overlapping, circular array in abutment with the valve seal. The overlapping arrangement allows the leaves to open upon insertion of an instrument. These approaches have been generally costly and complex.

Another problem with conventional devices has been the inability of the valve opening to align with the instrument if the instrument is inserted "off axis" (i.e., out of alignment with the throughbore in the valve seal). Attempts to resolve this problem have resulted in special mounting arrangements for the valve seal where the valve seal is laterally displaceable within a housing holding the valve seal. These solutions have required additional material and can be expensive and complex to implement.

By way of specific example, U.S. Pat. No. 5,147,336 to Antoon shows a trocar with a seal for sealing against surgical instruments of varying diameter to maintain insufflation in the body cavity. The seal has an elastomeric sealing component with a centrally located interior region containing an aperture, and a concentrically located sealing region. The sealing region is composed of an overlaying layer co-molded with an underlying layer. The overlaying layer has a hardness greater than that of the underlying layer. The seal is positioned between upper and lower rigid rings which divides the seal into inner and outer portions. The upper ring has a plurality of prongs which are fitted through the seal and are received in a plurality of receiving holes in the lower ring. The outer portion has a bellows configuration which facilitates the maintenance of a seal during radial motion of surgical instruments which are inserted into and withdrawn from the cannula. The seal assembly of Antoon, however, is difficult and costly to assemble. The seal assembly also requires prongs for support thus adding to the cost of the assembly. It also permits radial motion of the seal which may cause failure of the seal assembly.

The present invention is directed to overcoming one or more of the problems as set forth above.

SUMMARY OF THE INVENTION

In a first aspect of the present invention a surgical instrument seal assembly has an upper body portion having an upper surface that defines a throughbore extending completely through the seal assembly. A cylindrical wall protector extends inwardly into an interior portion of the upper body portion at the throughbore. A lower body portion projects below the upper body portion. The lower body portion defines a cannula receiving opening adapted to mount the seal assembly on the cannula. A valve seal is also provided which has an upper seal portion with a mounting portion mounted in the upper body portion adjacent an interior portion of the upper body portion. The upper seal portion is mounted about the throughbore. A lower seal portion extends from the upper seal portion and is adapted to seal around the surgical instrument.

In another aspect of the present invention, the seal assembly includes an upper body portion and a lower body portion projecting below the upper body portion. The valve assembly includes an upper seal portion mounted in the upper body portion and about a throughbore and a lower seal portion extending from the upper seal portion. The upper seal portion and/or the lower seal portion includes a reinforcing layer of woven material and an elastomeric material.

In yet another aspect of the present invention, the seal assembly is provided within a cannula. The cannula includes an upper housing and a lower elongated portion extending from the upper housing. The seal assembly is preferably housed within the upper housing.

BRIEF DESCRIPTION OF THE DRAWINGS

The foregoing and other objects, aspects and advantages will be better understood from the following detailed description of a preferred embodiment of the invention with reference to the drawings, in which:

FIG. 5 shows a perspective view the seal assembly within a cannula.

DETAILED DESCRIPTION OF A PREFERRED EMBODIMENT OF THE INVENTION

The present invention is directed to a valve seal assembly used with a cannula. The valve seal assembly is capable of providing a seal against leakage of fluid, gas and the like when an instrument is inserted therethrough. The valve seal assembly includes a durable puncture resistance reinforcing layer. The reinforcing layer ensures that an instrument will not puncture through the seal assembly during a surgical procedure thus causing fluid, gas and the like to leak therefrom. The reinforcing layer, much like the entire system, is easy and economical to manufacture. Also, the seal assembly of the present invention accommodates off axis alignment of the surgical instrument.

Surgical Seal Assembly of the Present Invention

Figure 1:
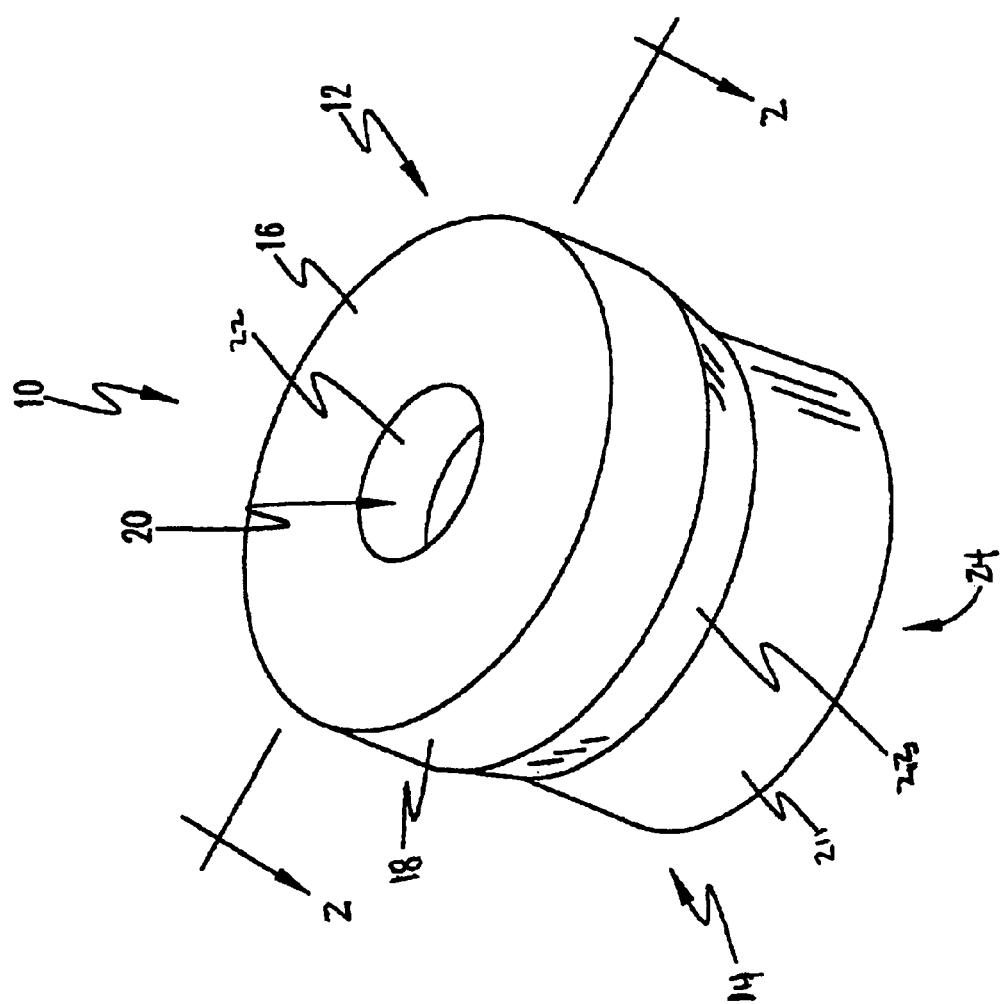
FIG. 1 is a perspective view of a a seal assembly according to an embodiment of the present invention.

Referring now to FIG. 1, a perspective view of a seal assembly is shown. The seal assembly is generally depicted as reference numeral 10 and includes an upper body portion 12 and a lower body portion 14. Both the upper and lower body portions 12 and 14 are generally cylindrical; however, the upper and lower body portions 12 and 14 may also be other cross sectional shapes which conform to a shape of a cannula or other surgical instrument. The upper body portion 12 includes a washer-shaped upper surface 16 having a generally cylindrical sidewall 18. A throughbore 20 is provided at the center of the washer-shaped upper surface 16 and extends through the seal assembly 10. A generally cylindrical wall member 22 is formed within the throughbore 20. The generally cylindrical wall member 22, in embodiments, projects into an interior portion of the upper body portion 12. Also, in embodiments, the generally cylindrical wall member 22 may be integrally formed with the washer-shaped upper surface 16. The generally cylindrical wall member 22 acts to strengthen the seal assembly 10 as well as guides a surgical instrument into the throughbore 20.

FIG. 1 further shows a generally cylindrical wall 21 forming the lower body portion 14. The generally cylindrical wall 21 extends below the upper body portion 12. A tapered transition wall 23 is disposed intermediate the cylindrical lower wall 21 and the upper body portion 12, and acts to taper the diameter of the seal assembly 10 from the larger upper body portion 12 to the smaller lower body portion 14. In embodiments, a stepped portion may be provided between the upper and lower portions 12 and 14. Alternatively, the upper and lower body portions 12 and 14 may be of the same or substantially the same size. A cannula receiving opening 24 is formed in the lower body portion 14 for mounting the device on a cannula (not shown). It should be recognized by those of ordinary skill in the art that the upper body portion 12, the transition wall 23, and the lower body portion 14 may be an integral assembly formed from molded polymeric or other similar material.

Figure 2:
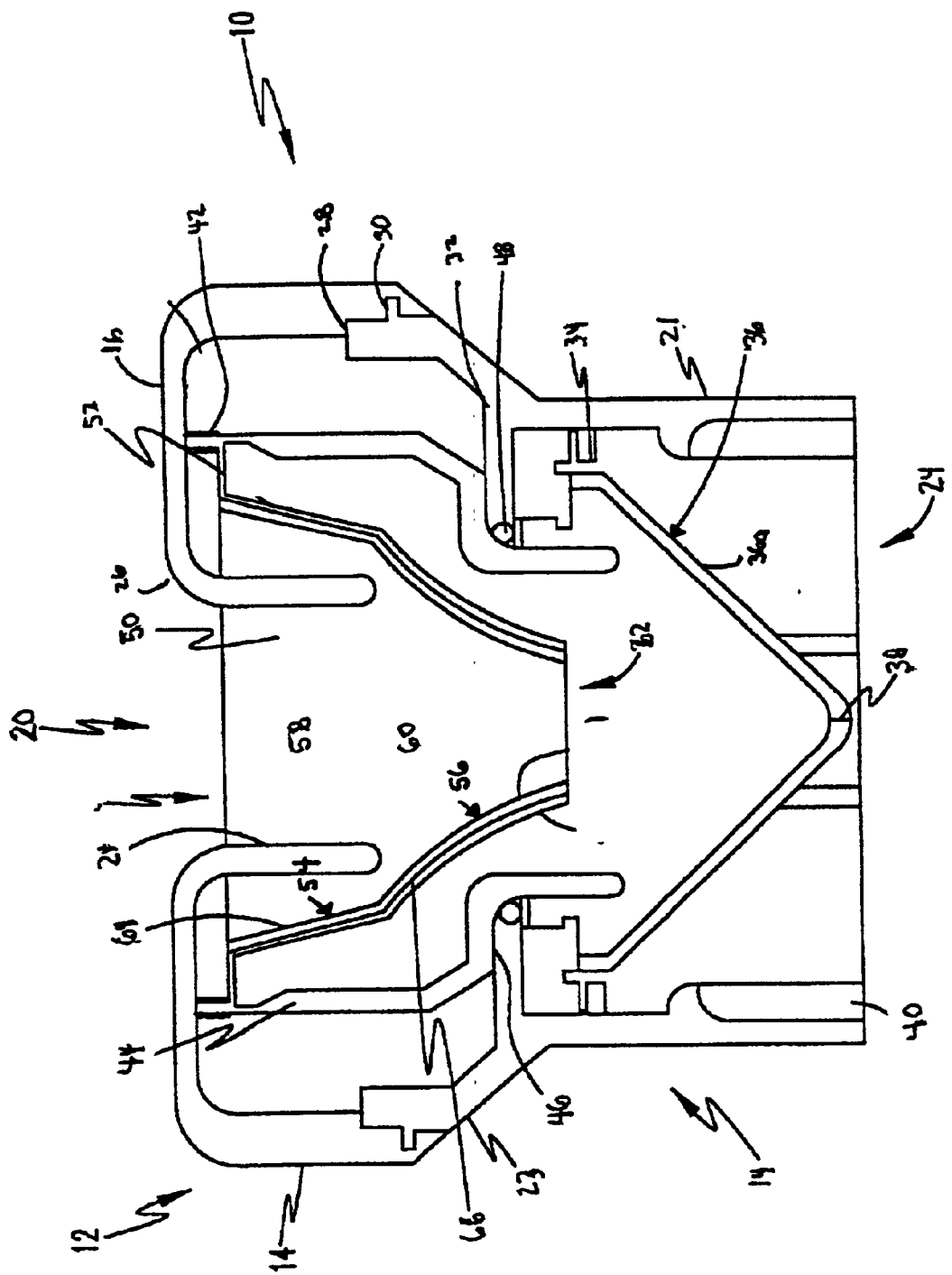
FIG. 2 is a cross-sectional view of the seal assembly illustrated in FIG. 1 along lines 2—2.

FIG. 2 is a cross-sectional view of the seal assembly 10 shown in FIG. 1. The upper body portion 12 includes the cylindrical wall member 22 which extends downward into an inner portion of the upper body portion 12. The cylindrical wall member 22 may be integrally formed with the washer-shaped upper surface 16, forming a smooth or curved transition 26 therebetween. The generally cylindrical sidewall 14 includes a shoulder 28 at a remote end, proximate to the transition wall 23. Likewise, the transition wall 23 also includes a shoulder or outwardly extending projection 30. In embodiments, the shoulder 28 of the generally cylindrical sidewall 14 mates with the shoulder 30 of the transition wall 22.

Still referring to FIG. 2, an inwardly extending projection 32 extends from the transition wall 23 (or the upper portion of the cylindrical wall 21 of the lower body portion 14), and the lower body portion 14 includes an inwardly extending lower mounting assembly 34. A duckbill valve assembly 36 is positioned between the inwardly extending projection 32 and the inwardly extending lower mounting assembly 34, and extends within the cannula receiving opening 24. In embodiments, the duckbill valve portion 36a of the duckbill valve assembly 36 is formed from an elastomeric member and includes a slit-like opening 38 that forms a seal. The slit-like opening 38 allows an instrument to be inserted through the cannula, as well as acts as an initial barrier to gases and fluids. The lower body portion 14 may also include mating members 40 which are designed to engage a cannula. The mating members 40 are preferably ribbed members which extend about an inner circumference of the lower body portion 14.

A mounting member 42 extends from an underside surface of the washer-shaped upper surface 16. An inner support member 44 projects downwardly from an interior portion of the upper body portion 12, opposite to the upper surface 16. Preferably, the inner support member 44 extends from the mounting member 42. The inner support member 44 includes a shoulder 46 which rests on the inwardly extending projection 32 of the transition wall 23. An o-ring 48 may be located between the shoulder 46 of the inner support member 44 and the inwardly extending projection 32 to form a substantially leak-tight seal between the upper body portion 12 and the lower body portion 14. The inner support member 44 may also provide stability for the seal assembly and a mounting location for a valve seal 50.

Turning now to the valve seal 50, a mounting portion 52 of the valve seal 50 is mounted to the upper body portion 12 at the mounting member 42 on the inner support member 44. The valve seal 50, including the mounting member 42 and the inner support member 44, may be a unitary assembly and rigidly mounted within the upper body portion 12. The valve seal 50 is preferably incapable of laterally shifting within the upper body portion 12 with respect to either the mounting member 42 or the inner support member 44.

The valve seal 50 is formed as a generally frusto-conical member having two portions defined by respective differently tapered walls. Specifically, the valve seal 50 is formed as an elastomeric member having a upper tapered portion 54 and a lower tapered portion 56. The lower tapered portion 56 is preferably sloped at a steeper angle than the upper tapered portion 54. Accordingly, an upper seal portion 58 of the valve seal 50 tapers from a relatively wide access opening to a lower seal portion 60. The lower seal portion 60 may also include, in embodiments, a curved slightly inwardly conical taper. An opening 62 is formed at the lower seal portion 60 of the valve seal 50, and is aligned with both the slit opening 38 of the duckbill assembly 36 and the bore 20. This construction allows the seal opening 62 to move radially, at least a small distance to accommodate an off axis instrument insertion.

The valve seal 50 further includes a reinforcement layer 64. The reinforcement layer 64 provides the flexibility necessary to expand the valve opening 58 yet protects the valve seal 50 from damage from a surgical instrument. Specifically, the reinforcement layer 64 may be formed, partly, from any elastomeric material which expands to accommodate a surgical instrument and forms a seal around the instrument to prevent leakage of fluids, gases and the like. The reinforcement layer 64 is preferably a layer of woven material such as fabric with nylon or spandex type material (stretchable material) encapsulated within silicon or other such elastomeric material. The reinforcing layer 64 and more specifically the woven material will provide a resilient and tear proof barrier for when the instrument is inserted within the seal; that is, the reinforcing layer 64 will provide protection against punctures by an instrument and resists inversion of the valve seal 50 when an instrument is withdrawn therefrom.

It should be noted that the valve seal 50 may be formed as a multilayered structure. In this embodiment, a second layer 66 may also be provided either above or below the reinforcing layer. In this manner, the reinforcing layer 64 may be the inner wall or the outer wall or may equally be sandwiched between two walls (not shown). The second layer 66 may be any elastomeric material which expands to accommodate a surgical instrument and forms a seal around the instrument to prevent leakage of fluids, gases and the like. The reinforcing layer 64 preferably stretches or moves proportionally with the elastomeric material layer 66 (e.g., silicon or other elastic material) when an instrument is inserted within the seal.

Figure 3:
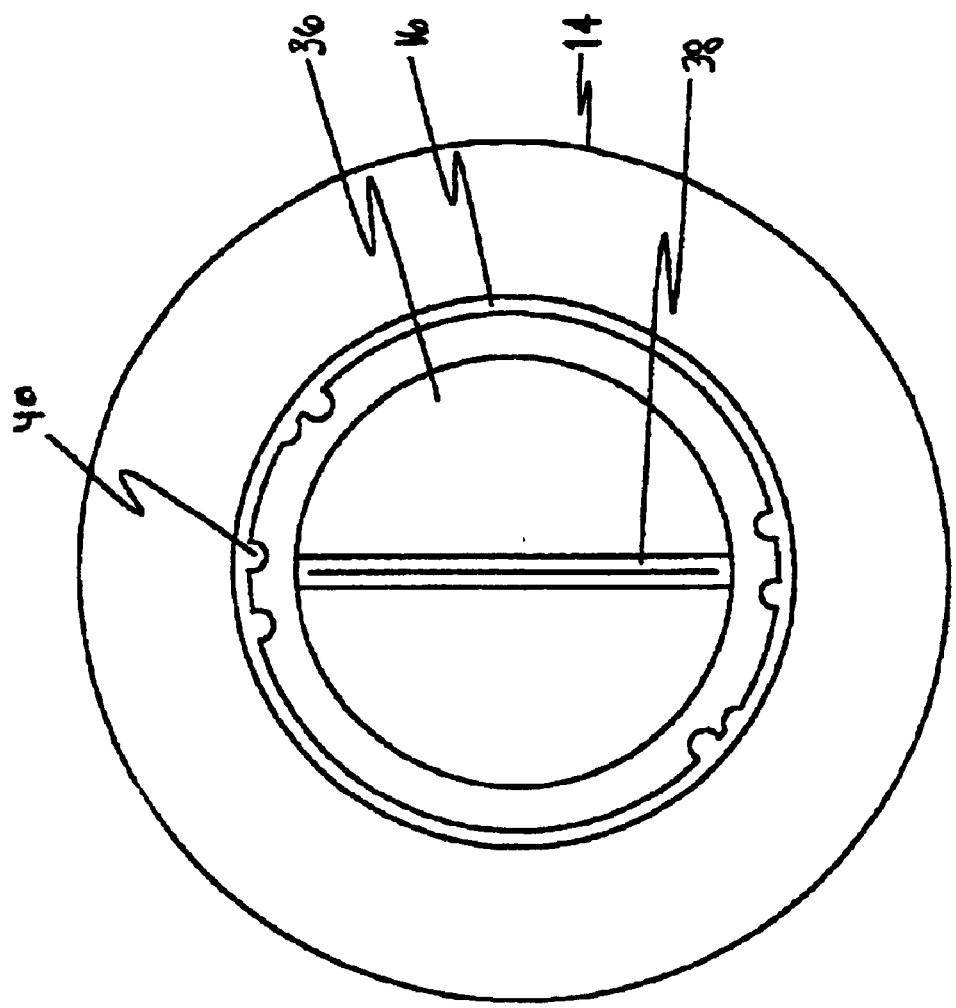
FIG. 3 is a bottom view of the seal assembly shown in FIG. 2.

FIG. 3 is a bottom view of the seal assembly shown in FIG. 2. In this figure, the mating members 40 are shown as ribbed members which extend about an inner circumference of the lower body portion 14. Also, the duckbill valve assembly 36 with the slit-like opening 38 is shown to be extending within the cannula receiving opening 24.

Figure 4:
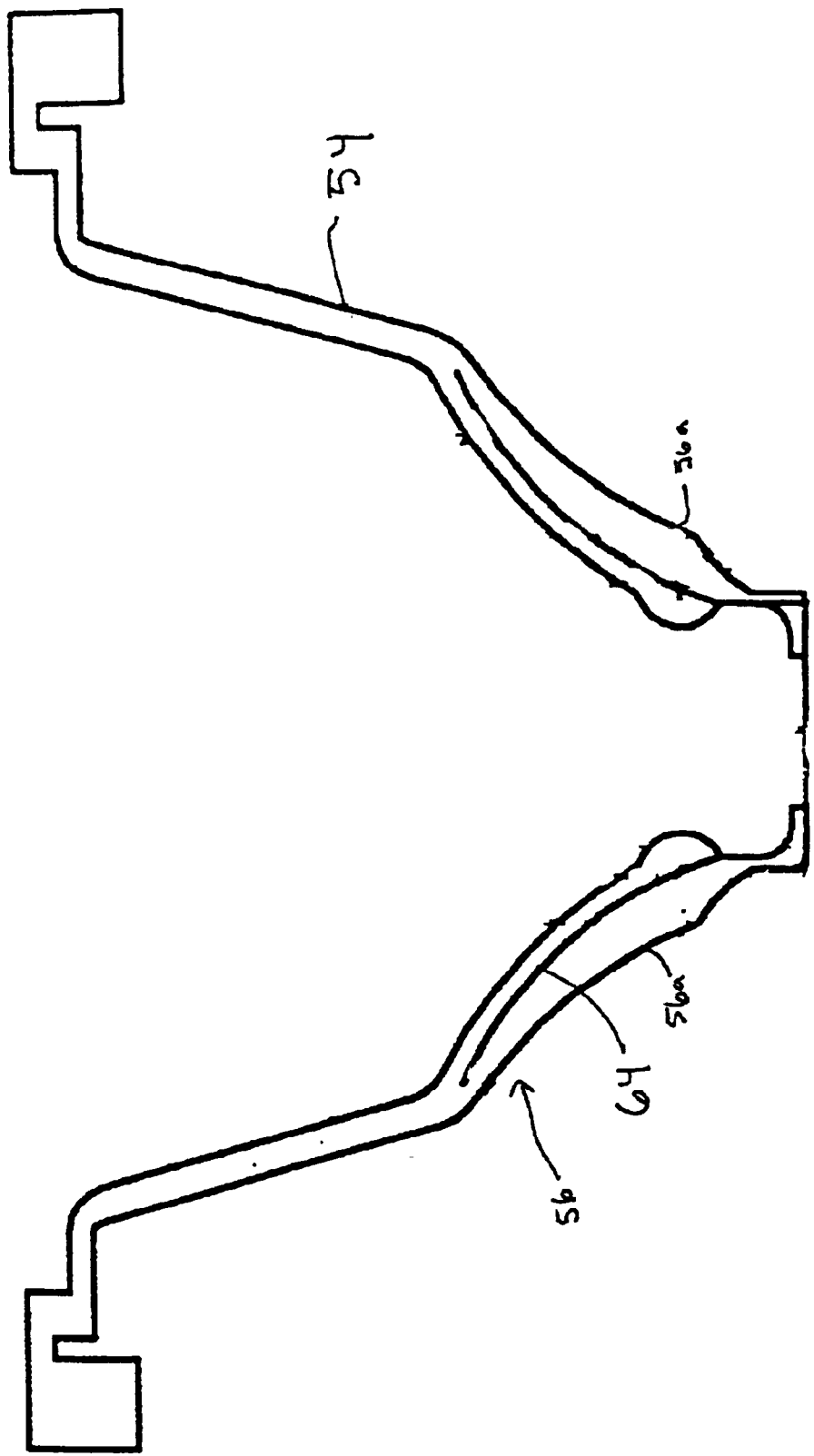
FIG. 4 is a cross-sectional view of the valve seal.

FIG. 4 shows a side view of the valve seal. In FIG. 4, the lower tapered portion 56 of the valve seal 50 includes a plurality of downward extending sections 56a. As further seen clearly in FIG. 4, the reinforcement layer 64 is positioned, in embodiments, in the lower tapered portion 56. The reinforcement layer 64 may also be positioned at the upper tapered portion 54, in embodiments. As discussed above, the reinforcement layer 64 may be formed from any elastomeric material which expands to accommodate a surgical instrument and forms a seal around the instrument to prevent leakage of fluids, gases and the like.

FIG. 5 shows the valve seal assembly of the present invention within a cannula 72. In one embodiment, the cannula 72 and the valve seal assembly is one integral unit. In embodiments, the cannula includes a lower stem portion 74 and an upper housing portion 76. The valve seal assembly of the present invention is preferably housed in the upper housing portion 76.

Method of Using the Surgical Seal Assembly of the Present Invention

In operation, the seal assembly of the present invention is mounted to a cannula using the mating members. A surgical instrument (not shown) is inserted into the throughbore for passage through the instrument seal opening and the duckbill valve. If the instrument is inserted off axis, the reinforcement layer of the valve seal resists puncture and the lower body portion allows some movement of the instrument seal opening to accommodate the insertion of the instrument. The curved taper of the lower seal portion helps to guide the instrument toward the instrument seal opening. In an exemplary embodiment, the lower seal portion has a curved taper from the bottom of the upper seal portion to the seal opening.

When the instrument passes through the instrument seal opening the elastomeric nature of the valve seal allows the opening to expand so as to accommodate the instrument. Typical openings may be 5 mm across in a relaxed state and may expand up to 12 mm to accommodate the instrument. It should be understood by those of ordinary skill in the art that other sized openings to accommodate various sizes of instruments is also contemplated by the present invention. The lower seal walls allow the instrument seal opening to fit snugly around the instrument to provide a fluid and gas seal. The instrument is then inserted through the duckbill valve The instrument may then be inserted downwardly into the cannula and, eventually, into the body cavity.

While the invention has been described in terms of preferred embodiments, those skilled in the art will recognize that the invention can be practiced with modification within the spirit and scope of the appended claims.

Having thus described our invention, what we claim as new and desire to secure by letters patent is as follows:

1. A seal assembly, comprising:

an upper body portion;

a lower body portion projecting below the upper body portion; and a valve seal comprising:
an upper seal portion mounted in the upper body portion and about a throughbore; and
a lower seal portion extending from the upper seal portion, the lower seal portion being adapted to seal around the surgical instrument,
wherein at least one of the upper seal portion and the lower seal portion includes a reinforcing layer of woven material encapsulated within an elastomeric material.

2. The seal assembly of claim 1, wherein:

the upper body portion includes an upper surface that defines a throughbore extending completely through the seal assembly;

the lower body portion defines a cannula receiving opening adapted to mount the seal assembly on the cannula; and the upper seal portion includes a mounting portion mounted in the upper body portion adjacent an interior portion of the upper body portion, the upper seal portion is mounted about the throughbore.

3. The seal assembly of claim 1, wherein:

the upper body portion further comprises an inner support member extending inwardly into the interior portion of the upper body; and the inner support member includes a shoulder.

4. The seal assembly of claim 3, further comprising a shoulder extending from a transition wall into an interior portion of the lower body portion, the shoulder of the transition wall mating with the shoulder of the inner support member.

5. The seal assembly of claim 1, wherein the upper seal portion includes a generally frusto-conical lower sealing member having a taper that is different from a taper of the lower seal portion.

6. The seal assembly of claim 1, wherein the woven material is expandable fabric.

7. The seal assembly of claim 6, wherein the woven material is encapsulated within the elastomeric material and expands proportionally with an insertion of an instrument.

* * * * *